United States Patent [19]
Loewy

[11] Patent Number: 5,914,229
[45] Date of Patent: Jun. 22, 1999

[54] METHOD FOR AMPLIFYING A POLYNUCLEOTIDE

[75] Inventor: Zvi Loewy, Fair Lawn, N.J.

[73] Assignee: Sarnoff Corporation, Princeton, N.J.

[21] Appl. No.: 08/663,688

[22] Filed: Jun. 14, 1996

[51] Int. Cl.$^6$ .................. C12Q 1/68; C12P 19/34
[52] U.S. Cl. ................... 435/6; 435/91.1; 435/91.2; 435/91.52
[58] Field of Search .................. 435/91.2, 91.52, 435/91.1, 6; 536/25.32, 25.5

[56] References Cited

U.S. PATENT DOCUMENTS

| | | | |
|---|---|---|---|
| 4,683,195 | 7/1987 | Mullis et al. | 435/6 |
| 5,143,854 | 9/1992 | Pirrung et al. | 436/518 |
| 5,194,370 | 3/1993 | Berninger et al. | 435/6 |
| 5,215,899 | 6/1993 | Dattagupta | 435/6 |
| 5,229,297 | 7/1993 | Schnipelsky et al. | 436/94 |
| 5,359,115 | 10/1994 | Campbell et al. | 558/110 |
| 5,369,003 | 11/1994 | Reischl et al. | 435/6 |
| 5,420,328 | 5/1995 | Campbell | 558/110 |
| 5,424,186 | 6/1995 | Fodor et al. | 435/6 |
| 5,527,670 | 6/1996 | Stanley | 435/6 |
| 5,545,522 | 8/1996 | Van Gelder | 435/6 |
| 5,595,879 | 1/1997 | Utermohlen | 435/6 |

FOREIGN PATENT DOCUMENTS

| | | |
|---|---|---|
| 0 320 308 | 6/1989 | European Pat. Off. . |
| 0 320308 | 6/1989 | European Pat. Off. . |
| 0 427 074 A2 | 5/1991 | European Pat. Off. . |
| WO 87/06270 | 10/1987 | WIPO . |
| WO 88/10315 | 12/1988 | WIPO . |
| WO 92/10092 | 6/1992 | WIPO . |
| WO 93/06121 | 4/1993 | WIPO . |
| WO 95/11996 | 5/1995 | WIPO . |

OTHER PUBLICATIONS

Harada, T. Diagnosis by recombinant DNA techniques and clinical features of familial amyloid polyneuropathy Brain Nerve vol. 40(7), pp. 617–621 (only Abstract), 1988.

*J. Virol. Methods,* vol. 43, pp. 177–188 (1993).

Ikeda et al., *Proc. Natl. Acad. Sci. USA,* 83, pp. 3614–3618, (1986).

Schenborn et al., *Nucleic Acids Research,* 13, No. 17, pp. 6223–6236, (1985).

Chapman et al., *Nucleic Acids Research,* 10, No. 20, pp. 6331–6340, (1982).

Chapman et al., *Nucleic Acids Research,* 15, No. 13, pp. 5413–5432, (1987).

*Primary Examiner*—Kenneth R. Horlick
*Attorney, Agent, or Firm*—William J. Burke

[57] ABSTRACT

In one aspect, the present invention relates to methods of amplifying a target nucleic acid, the methods involving the production of a double-stranded promoter to provide for transcription of the target sequence, and the provision of a poly-A tail in the transcription product. In another aspect, the present invention relates to methods of detecting a target nucleic acid in a sample.

30 Claims, No Drawings

METHOD FOR AMPLIFYING A POLYNUCLEOTIDE

RELATED CO-PENDING U.S. PATENT APPLICATIONS

This patent application is being concurrently filed with the following related U.S. patent applications: "Method for Polynucleotide Sequencing," R. Kumar and P. Heaney, inventors, Ser. No. 08/665,210, filed Jun. 14, 1996, abandoned; "Nuclease Protection Assays," R. Kumar, inventor, Ser. No. 08/665,104, filed Jun. 14, 1996, U.S. Pat. No. 5,770,370; "Microfluidic Method for Nucleic Acid Amplification," Z. Loewy and R. Kumar, inventors, Ser. No. 08/665,209, filed Jun. 14, 1996; "Automated Nucleic Acid Preparation" D. Southgate and Z. Loewy, inventors, Ser. No. 08/664,780, filed Jun. 14, 1996; and "Padlock Probe Detection," R. Kumar, inventor, Ser. No. 08/665,208, filed Jun. 14, 1996. This patent application is related to the following copending U.S. patent applications: Ser. No. 60/009517, filed Nov. 3, 1995; Ser. No. 60/00602, filed Nov. 3, 1995; and Ser. No. 60/010513, filed Jan. 24, 1996. All of the foregoing patent applications are hereby incorporated by reference herein in their entirety.

This invention was made with U.S. Government support under Contract No. 70NANB5H1037. The U.S. Government has certain rights in this invention.

The present invention relates to methods of amplifying a target nucleic acid, the methods involving the production of a double-stranded promoter to provide for transcription of the target sequence, and the provision of a poly-A tail in the transcription product.

Numerous methods of amplification are known in the art. Methods that include a transcription step can increase the amplified product by more than a factor of two at each cycle, and theoretically, more than a factor of 100 since 100 or more transcripts can be made from a single target nucleic acid. Further, amplifications that are based on transcription do not require thermo-cycling and therefore are much faster than amplification procedures that require thermo-cycling such as PCR.

In one aspect, the present invention provides an advantage over the transcription-based amplification procedures of the prior art, for example, by the combination of transcription amplification and target-specific ligation, thereby providing for greater specificity. In another aspect, the present invention provides an advantage over the prior art, for example, by providing a mechanism for readily identifying or isolating amplification products by providing a poly-A tail on the amplification products. Further, the methods of the invention provide an advantage over transcription-based amplification reactions of the prior art since the methods of the invention require fewer enzymes in the reactions.

SUMMARY OF THE INVENTION

In one aspect, the present invention provides methods of amplifying a target nucleic acid in a sample comprising the steps of:

(a) providing the target nucleic acid of the sample as single-stranded nucleic acid;

(b) combining with the sample at least one oligonucleotide, wherein the oligonucleotide or oligonucleotides include a double-stranded promoter, a single-stranded segment of nucleic acid complementary to a segment of the target nucleic acid, and a poly-T tail;

(c) annealing the oligonucleotide and the target nucleic acid to each other; and (d) adding an RNA polymerase and ribonucleoside triphosphates or analogs thereof.

In another aspect, the present invention provides a method of detecting a target nucleic acid in a sample comprising the steps of:

(a) providing the nucleic acid of the sample as single-stranded nucleic acid;

(b) combining with the sample at least one oligonucleotide, wherein the oligonucleotide or oligonucleotides include a double-stranded promoter, a single-stranded segment of nucleic acid complementary to a segment of the target nucleic acid, and a poly-T tail;

(c) contacting the oligonucleotide with the sample nucleic acid; and (d) adding an RNA polymerase and ribonucleoside triphosphates or analogs thereof.

Preferably, in the methods of the invention, steps (a) through (d) are repeated, preferably twice, thereby resulting in transcription amplification if the target polynucleotide is present in the sample, and the methods preferably further comprise the detection of the presence or absence of transcripts resulting from step (d).

Preferably, less than three enzymes are used in steps (a) through (c), and in certain preferred embodiments, one enzyme, namely RNA polymerase, is used in steps (a) through (c).

Numerous embodiments of the above methods are possible, as illustrated in the following description. For example, the double-stranded promoter in step (b) can be formed by two oligonucleotides, each of which is single-stranded and each of which includes a promoter sequence complementary to the other's promoter sequence. Alternatively, for example, the double-stranded promoter can be formed by a single nucleotide with a promoter in a double-stranded region of the nucleotide, such as a hairpin structure.

In further embodiments, the oligonucleotides in step (b) include at least two oligonucleotides having a sequence complementary to a sequence in the target nucleic acid, the sequences of the two oligonucleotides being contiguous in the target nucleic acid. The use of such oligonucleotides provides for the detection of the presence or absence of transcripts that correspond to different alleles or point mutations.

For example, if the target nucleic acid has a first and a second sequence on the same strand, the first and second sequences being contiguous; the methods of the invention can be used with at least three oligonucleotides in step (b), comprising:

(i) a first oligonucleotide including a promoter and a first segment of nucleic acid complementary to the first sequence on the target nucleic acid;

(ii) a second oligonucleotide including a segment of nucleic acid complementary to the promoter of the first oligonucleotide;

(iii) a the third oligonucleotide including a segment of nucleic acid complementary to the second sequence on the target nucleic acid and a poly-T tail. The first and third oligonucleotides having complementary contiguous sequences can be ligated together by a joining agent, such as ligase, cyanogen bromide, or carbodiimide. The oligonucleotides can be ligated before or after step (c) in which the target sequence is contacted with the oligonucleotides. Numerous oligonucleotides can be subjected to ligation to detect the presence or absence of numerous alleles or point mutations.

In performing an amplification, the target nucleic acid is denatured, if necessary, to form a single-stranded polynucleotide. When the oligonucleotides are annealed to a complementary single-stranded target nucleic acid, the second oligonucleotide anneals to the first oligonucleotide, thereby forming a double-stranded promoter. The first and the third oligonucleotides anneal to adjacent segments of the target nucleic acid. The first and third oligonucleotides are then ligated, and the complex is transcribed. Due to the presence of the poly-T tail in the third oligonucleotide, the transcript has a poly-A tail. The steps of denaturation, annealing, ligating and transcription can then be repeated to provide for amplification of the target nucleic acid.

In another embodiment, the oligonucleotides do not necessarily have contiguous complementary sequences and ligation need not be performed; the oligonucleotides of step (b) comprising:

(i) a first oligonucleotide that includes a promoter, a segment of nucleic acid complementary to a segment of the target nucleic acid, and a poly-T tail; and (ii) a second oligonucleotide that comprises a segment of nucleic acid complementary to the promoter.

Methods of the invention involving an oligonucleotide or oligonucleotides that can only be transcribed if annealed to the target sequence can be used with a promoter corresponding to an RNA polymerase that uses either a single-stranded substrate or a double-stranded substrate for transcription. The promoter can be any nucleic acid sequence (DNA or RNA) that corresponds with, and is recognized by a polymerase enzyme which binds to the promoter and thereby initiates 3'-5' transcription. RNA polymerases that can be used include RNA polymerases produced by bacteriophages, such as T7, T3 and SP6.

Preferably, in those embodiments in which the oligonucleotides could be used as a substrate for transcription by an RNA polymerase without the oligonucleotides having annealed to the target sequence, transcription of the oligonucleotides without the target sequence annealed thereto is avoided. Thus, in some embodiments of the invention, the RNA polymerase does not cause transcription from a substrate that is a single stranded polynucleotide, such as an *E. coli* polymerase, and the promoter is a lac promoter, for example. Alternatively, for example, the methods can include the addition of an agent that destroys single-stranded polynucleotide prior to step (d), and a bacteriophage or an *E. coli* RNA polymerase can be used.

Prior to transcription, the target nucleic acid or an oligonucleotide is converted, if necessary, from a double-stranded form to a single-stranded form. In certain embodiments, this conversion is accomplished by thermal means, wherein the melting temperature used in the thermal means is from about 90° C. to about 100° C. in the absence of formamide, or less than about 90° C. in the presence of formamide.

In other embodiments, the target nucleic acid or an oligonucleotide is converted from a double-stranded form to a single-stranded form by non-thermal means, for example, contacting the nucleic acid or the oligonucleotide with base or acid. Another non-thermal means for converting the oligonucleotide from double-stranded to single-stranded is strand separation based on electrostatic charge.

The methods of detection of transcripts include, in one embodiment, providing a label associated with the ribonucleoside triphosphates or analogs thereof and determining whether there is labeled ribonucleoside triphosphates or analogs thereof in a transcript. In another embodiment, transcripts are detected by detecting the presence or absence of a poly-A-containing polynucleotide, such as by providing oligo dT attached to a solid substrate; and detecting a label associated with the solid substrate. Alternatively, for example, transcripts can be detected by providing at least one of the oligonucleotides of step (b) with a label attached thereto. Labels that can be used in the detection methods of the invention include, for example, biotin, polyG, a fluorescent dye or a radioisotope.

DETAILED DESCRIPTION

In one aspect, the present invention is directed to methods of amplifying a target sequence in a sample. In one embodiment, the invention provides a method with steps comprising:

(a) providing the target nucleic acid of the sample as single-stranded nucleic acid;

(b) combining with the sample at least one oligonucleotide, wherein the oligonucleotide or oligonucleotides include a double-stranded promoter, a single-stranded segment of nucleic acid complementary to a segment of the target nucleic acid, and a poly-T tail;

(c) contacting the oligonucleotide and the target nucleic acid; and (d) adding an RNA polymerase and ribonucleoside triphosphates or analogs thereof.

Preferably, steps (a) through (d) are repeated at least once, and more preferably, twice, thereby resulting in transcription amplification if the target polynucleotide is present in the sample. Most preferably, steps (a) through (d) are repeated only as many times as necessary to result in a detectable signal if the target sequence is present in the sample.

The above-described amplification method of the invention can thus be used to detect the presence of a particular target sequences, and preferred methods of the invention include the detection of the presence or absence of transcripts resulting from step (d).

Thus, another aspect of the invention provides methods of detecting a target nucleic acid in the nucleic acid of a sample comprising the steps of (a) providing the nucleic acid of the sample as single-stranded nucleic acid;

(b) combining with the sample at least one oligonucleotide, wherein the oligonucleotide or oligonucleotides include a double-stranded promoter, a single-stranded segment of nucleic acid complementary to a segment of the target nucleic acid, and a poly-T tail;

(c) contacting the oligonucleotide with the sample nucleic acid; and (d) adding an RNA polymerase and ribonucleoside triphosphates or analogs thereof.

Detection of a target nucleic acid can be used, for example, for forensic purposes or for clinical purposes, such as to the presence or absence of detect genetic abnormalities or diseases.

Unlike transcription amplification methods of the prior art, the methods of the invention preferably require less than three enzymes, and can require as few as one enzyme, namely RNA polymerase. In contrast, transcription amplification methods of the prior art, such as NASBA (nucleic acid sequence based amplification) require reverse transcriptase, RNase H and RNA polymerase. See, for example, *J. Virol. Methods* 43:177–188, which incorporated by reference herein in its entirety. Preferably, the methods of the invention are performed under isothermal conditions, namely, the methods do not require a change of temperature conditions during each cycle of amplification.

The methods of the present invention can be combined with amplification methods of the prior art, including for example, PCR (polymerase chain reation), LCR (ligase chain reaction) and QβR (bacteriophage Qβ replicase).

Numerous embodiments of the above methods are possible, as illustrated in the following description. For example, the double-stranded promoter in step (b) can be formed by two oligonucleotides, each of which is single-stranded and each of which includes a promoter sequence complementary to the other's promoter sequence. Alternatively, for example, the double-stranded promoter can be formed by a single nucleotide with a promoter in a double-stranded region of the nucleotide, such as a hairpin structure. Preferably, the promoter is at least about 17 bases long, and more preferably, the promoter is about 20 bases long, and most preferably, the length of the promoter corresponds to the length of the promoter in the organism in which the promoter occurs naturally.

The poly-T tail can be single-stranded or double-stranded, and preferably, it is transcribed when the target sequence is present to form a poly-A tail in the transcripts. Preferably, the poly-T tail is about 20 bases long.

In further embodiments, the oligonucleotides in step (b) include at least two oligonucleotides having a sequence complementary to a sequence in the target nucleic acid, the sequences of the two oligonucleotides being contiguous in the target nucleic acid. The use of such oligonucleotides provides for the detection of the presence or absence of transcripts that correspond to different alleles or point mutations.

For example, if the target nucleic acid has a first and a second sequence on the same strand, the first and second sequences being contiguous; and the oligonucleotides in step (b) can comprise at least three oligonucleotides, and the methods of the invention can be used with (i) a first oligonucleotide including a promoter and a first segment of nucleic acid complementary to the first sequence on the target nucleic acid;

(ii) a second oligonucleotide including a segment of nucleic acid complementary to the promoter of the first oligonucleotide;

(iii) a the third oligonucleotide including a segment of nucleic acid complementary to the second sequence on the target nucleic acid and a poly-T tail. The first and third oligonucleotides having complementary contiguous sequences can be ligated together by a joining agent, such as ligase, cyanogen bromide, or carbodiimide. Ligation is defined herein as the formation of a 3',5'-phosphodiester bond that links two nucleotides, and a joining agent is defined herein as an agent capable of causing ligation; a joining agent can be an enzyme or a chemical.

The oligonucleotides can be ligated before or after step (c) in which the target sequence is contacted with the oligonucleotides. Numerous oligonucleotides can be subjected to ligation to detect the presence or absence of numerous alleles or point mutations. Furthermore, the length of the sequences of the oligonucleotides complementary to the target sequence can be increased to increase the specificity of detection. Such sequences can be, for example, 20–1,000 bases long, and are preferably about 20–200 bases long. Such sequences can be synthesized in smaller oligonucleotides and ligated together, if desired.

To illustrate, the following three oligonucleotides can be constructed for annealment to the target sequence is 5'-TACATTCCCAACCGCGTGGCACAA<u>CAACTGGCGGGCAAACAGTCGTTGCT</u>-3' (SEQ ID NO: 1). The first oligonucleotide can be, for example, 5'-TTGTGCCACGCGGTTGGGAATGTA<u>TCTCCCTATAGTGAGTCGTATTAATTC</u>-3' (SEQ ID NO: 2), the underlined portion representing a T7 bacteriophage promoter, the remainder of the oligonucleotide being complementary to bold portion of the target. The second nucleotide is 5'-GAATTAATACGACTCACTATAGGGAGA-3' (SEQ ID NO: 3), which is complementary to the promoter in the first nucleotide. The third nucleotide is 5'-TTTTTTTTTTTTTTTTTTTTAGCAACGACTGTTTG-CCCGCCAGTTG-3' (SEQ ID NO: 4), having 20 deoxythimidines forming a poly-T tail, the remainder of the oligonucleotide being complementary to the underlined portion of the target.

In another embodiment, the oligonucleotides do not necessarily have contiguous complementary sequences and ligation need not be performed; the oligonucleotides of step (b) comprising:

(i) a first oligonucleotide that includes a promoter, a segment of nucleic acid complementary to a segment of the target nucleic acid, and a poly-T tail; and (ii) a second oligonucleotide that comprises a segment of nucleic acid complementary to the promoter.

Referring to the target sequence above, the first oligonucleotide can be, for example, 5'-T<u>TTTTTTTTTTTTTTTTTTT</u>AGCAACGACTGTTTGCCCGCCAGTTGTTGTGCCACGCGGTTGGGAATGTATCTCCCTATAGTGAGTCGTATTAATTC-3', (SEQ ID NO: 5), and the second oligonucleotide can be the same as the second oligonucleotide above. The underlined portion of SEQ ID NO: 5 oligonucleotide corresponds to the third oligonucleotide in the preceeding illustration, and the bold portion corresponds to the first oligonucleotide in the preceeding illustration. Alternatively, for example, the promoter portion of the first oligonucleotide can be double-stranded, thereby obviating the need for the second oligonucleotide.

In performing an amplification, the target nucleic acid is denatured, if necessary, to form a single-stranded polynucleotide. When the oligonucleotides are annealed to a complementary single-stranded target nucleic acid, the second oligonucleotide anneals to the first oligonucleotide, thereby forming a double-stranded promoter. The first and the third oligonucleotides anneal to adjacent segments of the target nucleic acid. The first and third oligonucleotides are then ligated, and the complex is transcribed. Due to the presence of the poly-T tail in the third oligonucleotide, the transcript has a poly-A tail. The steps of denaturation, annealing, ligating and transcription can then be repeated to provide for amplification of the target nucleic acid.

In another embodiment, the oligonucleotides do not necessarily have contiguous complementary sequences and ligation need not be performed; the oligonucleotides of step (b) comprising:

(i) a first oligonucleotide that includes a promoter, a segment of nucleic acid complementary to a segment of the target nucleic acid, and a poly-T tail; and (ii) a second oligonucleotide that comprises a segment of nucleic acid complementary to the promoter.

Methods of the invention involving an oligonucleotide or oligonucleotides that can only be transcribed if annealed to the target sequence can be used with a promoter corresponding to an RNA polymerase that uses either a single-stranded substrate or a double-stranded substrate for transcription. The promoter can be any nucleic acid sequence (DNA or RNA) that corresponds with, and is recognized by a polymerase enzyme which binds to the promoter and thereby initiates 3'-5' transcription. RNA polymerases that can be used include RNA polymerases produced by bacteriophages, such as T7, T3 and SP6.

Preferably, in those embodiments in which the oligonucleotides could be used as a substrate for transcription by an RNA polymerase without the oligonucleotides having annealed to the target sequence, transcription of the oligonucleotides without the target sequence annealed thereto is avoided. Thus, in some embodiments of the invention, the RNA polymerase does not cause transcription from a substrate that is a single stranded polynucleotide, such as an *E. coli* polymerase, and the promoter is a lac promoter, for example. Alternatively, for example, the methods can include the addition of an agent that destroys single-stranded polynucleotide prior to step (d), such as S1 nuclease, and a bacteriophage or an *E. coli* RNA polymerase can be used thereafter since only those oligonucleotides annealed to the target sequence will be transcribed under these conditions.

Prior to transcription, the target nucleic acid or an oligonucleotide is converted, if necessary, from a double-stranded form to a single-stranded form. In certain embodiments, this conversion is accomplished by thermal means, wherein the melting temperature used in the thermal means is from about 90° C. to about 100° C. in the absence of formamide, or less than about 90° C. in the presence of formamide.

In other embodiments, the target nucleic acid or an oligonucleotide is converted from a double-stranded form to a single-stranded form by non-thermal means, for example, contacting the nucleic acid or the oligonucleotide with base or acid. The base or acid is preferably removed prior to step (c). The removal can be accomplished, for example, by the addition of a solid substrate having releasable affinity for the oligonucleotides and the target nucleic acid, such that the solid substrate-oligonucleotide or -target nucleic acid complex is moved from denaturing to non-denaturing or non-denaturing to denaturing conditions.

Another non-thermal means for converting the oligonucleotide from double-stranded to single-stranded is separation based on electrostatic charge. For example, after an initial strand separation, one DNA strand is attached to a microparticle having a positive electrostatic charge and the other DNA strand is attached to a microparticle having a negative electrostatic charge. Thereafter, to separate the two strands, an electrostatic field is applied whereby one strand is electrostatically separated from the other. This method is particularly preferred since it does not require the use of heat or a denaturing agent, and can be accomplished simply by the application of an electric field. See, for example, "Microfluidic Method for Nucleic Acid Amplification," Z. Loewy and R. Kumar, inventors, Ser. No. 08/665,209, filed Jun. 14, 1996.

Transcription is initiated by addition of polymerase and the required rNTPs to the mixture that contains the target sequence and the oligonucleotides. Under suitable conditions, the synthesis of RNA transcripts will proceed in a continuous manner providing that sufficient amounts of rNTPs are present. Normally, a ribonuclease inhibitor will be included in the transcription reaction mixture in order to avoid undesirable degradation of RNA transcripts by any ribonuclease contamination. Transcription is allowed to proceed for a predetermined period of time until a detectable or desirable amount of RNA transcript has accumulated. The accumulated transcription product thus serves as an amplification of the target sequence. Transcription can then be terminated by any conventional means such as inactivation of the polymerase or removal of reactants from the mixture.

The detection of the presence or absence of transcripts can be accomplished in numerous ways. For example, in some embodiments, the detection involves detecting the presence or absence of a poly-A-containing polynucleotide. This can be accomplished, for example, by (i) providing oligo dT attached to a solid substrate; and (ii) detecting a label associated with the solid substrate.

The transcription products may be bound to the solid substrate by any stable interaction, including a hydrophobic, electrostatic or covalent interaction. The oligo dT, an oligonucleotide comprised of multiple deoxythimidines, preferably has about 20 to about 25 thymidines therein. For example, the solid substrate can be a paramagnetic bead, such as a bead about 2.8 microns in diameter comprised of iron dispersed in a polystyrene matrix, together with an oligo-dT, which can be obtained from Dynal (Oslo, Norway).

In other detection methods, the ribonucleoside triphosphates or analogs thereof include a label, and the detection involves determining the presence or absence of labeled ribonucleoside triphosphates or analogs thereof in a transcript. Thus, detection can be accomplished, for example, through the use of labeled rNTPs, separation of labeled transcription product and unused labeled rNTPs, and detection of the label in the transcription product if there is a positive result. Alternatively, for example, detection can be achieved through detection of a transcript, by separating RNA or destroying unreacted rNTPs and adding the bioluminescent reactants firefly luciferase, pyruvate kinase and polynucleotide phosphorylase. Further, detection of transcripts can be accomplished, for example, through the use of gel electrophoresis based on the known size of the transcript.

Detection can also be accomplished, for example, by hybridization of the transcription product with a labeled nucleic acid probe. Further, detection can be achieved through the use of an anti-hybrid reagent, including anti-DNA/RNA, anti-RNA/RNA or anti-DNA/DNA antibodies.

Labels that can be used in the methods of the invention include, for example, biotin, polyguanidine, a fluorescent dye or a radioisotope. Another means of detection is the use of energy transfer from an emitter to a donor dye, the energy transfer taking place only if the oligonucleotide containing the emitter is ligated to the oligonucleotide containing the donor dye. Further, detection can be accomplished, for example, using fluorophores, chemiluminescent compounds and chromophores. Alternatively, for example, a hapten which can bind to an antibody, a protein or enzyme can be used as a label.

Methods of attaching labels (i.e., reporter molecules) to polynucleotides are also well known in the art. For instance, Biosearch Products of PerSeptive Biosystems (Framingham, Ma.) markets 5' linker groups that are compatible with phosphoramidite chemistry. One of these groups includes a six-carbon spacer and a terminal amine that is protected with a trifluoroacetyl ("TFAc"). The TFAc protecting group is base-label and is removed during the normal post-synthesis workup of an oligonucleotide synthesized by the phosphoramidite method, which workup involves hydrolysis in the presence of ammonium hydroxide. Another amine-containing linker from this company also has a six-carbon spacer group and has the amine protected with a methoxytrityl ("MMT") group. The MMT group is acid-label, requiring a separate deprotection step. Both of these amine linkers can be used to attach molecules such as biotin or fluorescein. These amine spacer groups can also be used to attach other molecules having a free acid that can be used to form an amide with the amine group through a condensation reaction. Another linker from Biosearch Products has a six-carbon spacer with a thiol group protected by a trityl group. The trityl protecting group is removed by treatment with silver nitrate and dithiothreitol. This linker can be used to attach enzymes and molecules that incorporate maleimide. Methods to couple multiple labels can include the attachment of a polymer having a number of reactive sites, such as a number of amino or thiol groups, which reactive sites can be used to attach label. Labelling methods are described in: Sinha and Striepeke, "Oligonucleotides with Reporter Groups Attached to the 5' Terminus" in Oligonucleotides and Analogues: A Practical Approach, Eckstein, Ed., IRL, Oxford, 1991, p. 185 et seq.; Sinha and Cook, "The Preparation and Application of Functionalized Synthetic Oligonucleotides: 3. Use of H-Phosphate Derivatives of Protected Amino-Hexanol and Mercapto-Propanol or Mercapto-Hexanol," Nucleic Acids Research, 1988, Vol. 16, p. 2659 et seq.; Haugland, Molecular Probes Handbook of Fluorescent Probes and Research Chemicals, Molecular Probes, Inc., Eugene, Oreg., 1992, p. 20 et seq.; Theisen et al., "Fluorescent Dye Phosphoramidite Labelling of Oligonucleotides," Tetrahedron Letters, 1992, Vol. 33, p. 3036 et seq.; Rosenthal and Jones, "Genomic Walking and Sequencing by Oligocassette Mediated Polymerase Chain Reaction," Nucleic Acids Research, 1990, Vol. 18, p. 3095 et seq.; Smith et al., "The Synthesis of Oligonucleotides containing an Aliphatic Amino Group at the 5' Terminus— Synthesis of Fluorescent DNA Primers for Use in DNA-Sequence Analysis," Nucleic Acids Research, 1985, Vol. 13, 2399 et seq.

The detection used in conjunction with the invention will depend on the nature of the label. Where a colorimetric or fluorescent label is used visual inspection or an optical instrument such as the fluorescence microscope from Olympus (Lake Success, N.Y.), the Plate Reader device from BioTek Instruments (Winooski, Vt.) and the CCD (charge-coupled device) camera from Princeton Instruments (Princeton, N.J.). Where radioisotopes are used, detection can comprise such spatially sensitive detection devices as the Phosphor Imager device (Molecular Dynamics, Sunnyvale, Calif.), or can comprise separately detecting individual solid surfaces in a detection apparatus such as a gamma-counter or a liquid scintillation counter.

Reaction conditions and other information for use in the methods of the invention can be found, for example, in U.S. Pat. No. 5,215,899 (transcription amplification), U.S. Pat. No. 5,194,370 (transcription amplification), U.S. Pat. No. 4,683,195 (polymerase chain reaction), EP 0 320 308 (ligase chain reaction), WO 95/11996 (polymerase chain reaction-coupled ligase chain reaction), WO 88/10315 (transcription-based amplification), WO 87/06270 (Qβ replicase) and Maniatis et al., Molecular Cloning (Cold Spring Harbor 1982), all of which are hereby incorporated by reference herein in their entirety. Additionally, where methodologies are referred to herein without specific enumeration of well-known methods steps, generally, the following text can be referenced for further details: Ausubel et al., Short Protocols in Molecular Biology; Sambrook et al., DNA Cloning, A Laboratory Manual; and Molecular Biology Protocols, website: listeria.nwfsc.noaa.gov/protocols.html.

Methods of synthesizing nucleic acid probes are well known in the art. Such methods are reviewed for example in Caruthers, Science 230: 281–285, 1985; Itakura et al., Ann. Rev. Biochem. 53: 323–356; Hunkapillar et al., Nature 310: 105–110, 1984; and in "Synthesis of Oligonucleotide Derivatives in Design and Targeted Reaction of Oligonucleotide Derivatives, CRC Press, Boca Raton, Fla., pages 100 et seq. The phosphoramidite and phosphite triester approaches are most broadly used, but other approaches include the phosphodiester approach, the phosphotriester approach and the H-phosphonate approach.

In preferred embodiments, the methods of the invention are used in the context of a microfluidics-based device for automatedly moving fluids in and out of a reaction chamber, which has been disclosed in U.S. patent Ser. No. 60/010513, filed Jan. 24, 1996, the contents of which are incorporated herein by reference. The microfluidics device is designed specifically for moving small volumes of fluids through fluid exchange channels that connect various sorts of fluid chambers. In particular, such a device comprises a fluid chamber, which is a generic term that describes chambers designed for storage of fluid reagents or reactants, i.e., a supply chamber, for locating reactants undergoing a reaction, i.e., a reaction chamber, for measuring a volume of a fluid, i.e., a metering chamber, and more. More particularly, the inventive device includes a reaction chamber wherein, for example, suitable means are employed for amplifying nucleic acid in the reaction chamber. The reaction chamber is comprised of any suitable material, as are all fluid chambers, such as, for example, glass, plastic, ceramic, or combinations thereof, and is connected to at least two fluid exchange channels for passaging material in and out of the reaction chamber. The reaction chamber preferably remains at a constant temperature of within about two degrees centigrade, wherein the temperature is between about 20° C. and 65° C., and alternatively can have adjustable temperatures as in accordance with the requisites of the reactions to take place therein. The reactions can take place on a solid surface such as a microparticle, and more preferably a paramagnetic microparticle. The reaction chamber can be the site at which the detection methods described hereinabove take place.

The liquid distribution system can conduct synthesis in a great number of separate reaction wells, such as 10,000 reaction wells. The synthesis in each reaction well can occur on a bead or microparticle or can occur on the surfaces of the wells, where these surface, have been appropriately treated. The wells are formed on a plate that is separable from the portions of the liquid distribution system used to shuttle reagents to a multitude of reaction wells. Another way of forming an array is to apply the photolithographic synthesis procedures described in a number of patents and patent applications owned by Affymax, Inc. These include Fodor et al., "Very Large Scale Immobilized Polymer Synthesis," WO92/10092; Dovor et al., "Method of Synthesizing Diverse Collections of Oligomers," WO93/06121; Campbell et al., "Methods for Synthesis of Phosphonate Esters," U.S. Pat. No. 5,359,115; Campbell, "Methods for Synthesis of Phosphonate Esters," U.S. Pat. No. 5,420,328; Fodor et al., "Very Large Scale Immobilized Polymer Synthesis," U.S. Pat. No. 5,424,186; and Pirrung et al., "Large Scale Photolithographic Solid Phase Synthesis of Polypeptides and Receptor Binding Screening Thereof," U.S. Pat. No. 5,143, 854.

A microparticle can have any shape, and preferably it is spherical. Preferably, it has a diameter of less than 1 mm, and more preferably, less than 500 microns. In certain prefererred embodiments, the microparticles have a diameter from about 0.5 micron to about 25 microns, and more preferably about 1 micron to about 5 microns, and even more preferably, about 2 microns to about 4 microns. Microparticles are comprised of any suitable material, the choice of material being guided by its characteristics, which preferably include minimal non-specific absorptive characteristics, such as that of polystyrene. In other embodiments, the microparticles are comprised of, for example, plastic, glass, cellulose, a cellulose derivative, nylon, polytetrafluoroethylene ("TEFLON"), ceramic and the like. A paramagnetic bead can be comprised of, for example, iron dispersed in a polystyrene matrix, and can be obtained with an associated biomolecule such as oligo-dT, for example, from Dynal (Oslo, Norway), or without an associated biomolecule, for example, from Bang Laboratories (Carmel, Ind.).

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

---

What is claimed:

1. A method of amplifying a target nucleic acid in a sample comprising the steps of:
   (a) providing the target nucleic acid of the sample as single-stranded nucleic acid;
   (b) combining with the sample at least one oligonucleotide, wherein the oligonucleotide or oligonucleotides include a double-stranded promoter, a single-stranded segment of nucleic acid complementary to a segment of the target nucleic acid, and a homopolynucleotide;
   (c) annealing oligonucleotide(s) comprising the double-stranded promoter, complementary segment and homopolynucleotide to the target nucleic acid; and
   (d) adding an RNA polymerase and ribonucleoside triphosphates or analogs thereof, thereby generating transcripts.

2. The method of claim 1, further comprising repeating steps (a) through (d) at least twice.

3. The method of claim 1, further comprising detection of the presence or absence of the transcripts resulting from step (d).

4. The method of claim 3, wherein the ribonucleoside triphosphates or analogs thereof include a reporter molecule, and the method further comprises detection of the presence or absence of the reporter molecule, wherein the reporter molecule comprises biotin, poly G, a fluorescent dye, or a radioisotope.

5. The method of claim 3, further comprising detection of the presence or absence of the homopolynucleotide or a complement thereof.

6. A method of amplifying a target nucleic acid in a sample comprising the steps of:
   (a) providing the target nucleic acid of the sample as single-stranded nucleic acid;
   (b) combining with the sample at least one oligonucleotide, wherein the oligonucleotide or oligonucleotides include a double-stranded promoter, a single-stranded segment of nucleic acid complementary to a segment of the target nucleic acid, and a homopolynucleotide;
   (c) annealing oligonucleotide(s) comprising the double-stranded promoter, complementary segment and homopolynucleotide the target nucleic acid;
   (d) adding an RNA polymerase and ribonucleoside triphosphates or analogs thereof, thereby generating the complement of the complementary segment and homopolynucleotide, and
   (e) detecting the complementary polynucleotide which is produced as a transcript in step (d), and wherein detection comprises:
      (i) providing the homopolynucleotide attached to a solid substrate;
      (ii) combining the substrate-attached homopolynucleotide and the polynucleotide to be detected under conditions that promote hybridization therebetween; and
      (iii) detecting the polynucleotide to be detected associated with the solid substrate.

7. The method of claim 1, wherein at least one of the oligonucleotides of step (b) has a reporter molecule attached thereto which is annealed to the target nucleic acid.

8. The method of claim 4, wherein the reporter molecule comprises the fluorescent dye or the radioisotope.

9. The method of claim 1, wherein the double-stranded promoter comprises two oligonucleotides, each of which is single-stranded and each of which includes a promoter sequence complementary to the other's promoter sequence.

10. The method of claim 1, wherein the double-stranded promoter comprises a single polynucleotide with a promoter in a double-stranded region of the polynucleotide.

11. The method of claim 10, wherein the double-stranded region consists of a hairpin structure.

12. A method of amplifying a target nucleic acid in a sample comprising the steps of:
   (a) providing the target nucleic acid of the sample as single-stranded nucleic acid;
   (b) combining with the sample at least one oligonucleotide, wherein the oligonucleotide or oligonucleotides include a double-stranded promoter, a single-stranded segment of nucleic acid complementary to a segment of the target nucleic acid, and a homopolynucleotide;
   (c) annealing oligonucleotide(s) comprising the double-stranded promoter, complementary segment and homopolynucleotide to the target nucleic acid; and
   (d) adding an RNA polymerase and ribonucleoside triphosphates or analogs thereof, thereby generating the complement of the complementary segment and homopolynucleotide,
   wherein the target nucleic acid has a first and a second sequence on the same strand, said first and second sequences being contiguous; and wherein the oligonucleotides in step (b) comprises at least three oligonucleotides, the three oligonucleotides comprising:
      (i) a first oligonucleotide including a promoter and a first segment of nucleic acid complementary to the first sequence on the target nucleic acid;
      (ii) a second oligonucleotide including a segment of nucleic acid complementary to the promoter of the first oligonucleotide;
      (iii) and a third oligonucleotide including a segment of nucleic acid complementary to the second sequence on the target nucleic acid and the homopolynucleotide.

13. The method of claim 12, wherein the promoter is a bacteriophage promoter.

14. The method of claim 1 wherein the oligonucleotides in step (b) include at least two oligonucleotides having a sequence complementary to a sequence in the target nucleic acid, the sequences of the two oligonucleotides being contiguous in the target nucleic acid.

15. The method of claim 14, wherein the amplification of the target nucleic acid includes detection of transcripts, said detection being used to determine presence or absence of at least one allele or a point mutation in the target nucleic acid.

16. The method of claim 14 wherein the oligonucleotides having complementary contiguous sequences are ligated together by a joining agent.

17. The method of claim 16 wherein ligation occurs prior to step (c).

18. The method of claim 16 wherein ligation occurs after step (c).

19. The method of claim 16, wherein the joining agent is ligase, cyanogen bromide, or carbodiimide.

20. The method of claim 1 wherein the RNA polymerase does not cause transcription from a substrate that is a single stranded polynucleotide.

21. The method of claim 20 wherein the RNA polymerase is an *E. coli* polymerase.

22. The method of claim 1 further comprising the addition of an agent that destroys single-stranded polynucleotide prior to step (d).

23. The method of claim 1 wherein the promoter is a lac promoter.

24. The method of claim 1 wherein the oligonucleotides of step (b) comprise:
   (i) a first oligonucleotide that includes a promoter, a segment of nucleic acid complementary to a segment of the target nucleic acid, and the homopolynucleotide; and
   (ii) a second oligonucleotide that comprises a segment of nucleic acid complementary to the promoter.

25. The method of claim 1, wherein the target nucleic acid or an oligonucleotide is converted from a double-stranded form to a single-stranded form by thermal means, wherein the melting temperature used in the thermal means is from about 90° C. to about 100° C. in the absence of formamide, or less than about 90° C. in the presence of formamide.

26. The method of claim 1, wherein the target nucleic acid or an oligonucleotide is converted from a double-stranded form to a single-stranded form by non-thermal means.

27. The method of claim 26, wherein the non-thermal means includes contacting the nucleic acid or the oligonucleotide with base or acid.

28. The method of claim 26, wherein the non-thermal means includes use of electrostatics.

29. The method of claim 6, wherein the solid substrate is a paramagnetic bead.

30. A method of detecting a target nucleic acid in a sample comprising the steps of:
   (a) providing the nucleic acid of the sample as single-stranded nucleic acid;
   (b) combining with the sample (i) at least one first oligonucleotide, wherein the at least one first oligonucleotide can form a double-stranded promoter which is joined to a first single-stranded segment of nucleic acid complementary to a first segment of the target nucleic acid, and (ii) a second oligonucleotide that includes a second single-stranded segment of nucleic acid complementary to a second segment of the target nucleic acid which is adjacent to the first segment of the target nucleic acid, wherein the second oligonucleotide comprises a homopolynucleotide label;
   (c) contacting the oligonucleotides comprising the first and second single-stranded segments with the sample nucleic acid and, if the target nucleic acid is present, ligating the first and second single-stranded segments; and
   (d) forming the double-stranded promoter and, if the ligation of step (c) has occurred, catalyzing with an RNA polymerase the formation of a nucleic acid segment complementary to the first and second single-stranded segments and the homopolynucleotide label.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 50 base pairs
       (B) TYPE: nucleic acid
       (C) STRANDEDNESS: double
       (D) TOPOLOGY: linear (xi) SEQUENCE DESCRIPTION: SEQ ID NO:1:

TACATTCCCA ACCGCGTGGC ACAACAACTG GCGGGCAAAC AGTCGTTGCT          50

(2) INFORMATION FOR SEQ ID NO:2:

(i) SEQUENCE CHARACTERISTICS:
       (A) LENGTH: 51 base pairs
       (B) TYPE: nucleic acid
       (C) STRANDEDNESS: single
       (D) TOPOLOGY: linear (xi) SEQUENCE DESCRIPTION: SEQ ID NO:2:

TTGTGCCACG CGGTTGGGAA TGTATCTCCC TATAGTGAGT CGTATTAATT C          51

(2) INFORMATION FOR SEQ ID NO:3:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (xi) SEQUENCE DESCRIPTION: SEQ ID NO:3:

GAATTAATAC GACTCACTAT AGGGAGA          27

(2) INFORMATION FOR SEQ ID NO:4:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (xi) SEQUENCE DESCRIPTION: SEQ ID NO:4:

TTTTTTTTTT TTTTTTTTTT AGCAACGACT GTTTGCCCGC CAGTTG          46

(2) INFORMATION FOR SEQ ID NO:5:

(i) SEQUENCE CHARACTERISTICS:
       (A) LENGTH: 97 base pairs
       (B) TYPE: nucleic acid
       (C) STRANDEDNESS: single
       (D) TOPOLOGY: linear (xi) SEQUENCE DESCRIPTION: SEQ ID NO:5:

TTTTTTTTTT TTTTTTTTTT AGCAACGACT GTTTGCCCGC CAGTTGTTGT GCCACGCGGT          60

TGGGAATGTA TCTCCCTATA GTGAGTCGTA TTAATTC                                  97